United States Patent
Surushe et al.

(10) Patent No.: US 12,419,793 B2
(45) Date of Patent: Sep. 23, 2025

(54) ABSORBENT ARTICLE COMPRISING A MULTI-LAYER CUSHION LAYER

(71) Applicant: The Procter & Gamble Company, Cincinnati, OH (US)

(72) Inventors: Abhishek Prakash Surushe, Kelkheim (DE); Ernesto Gabriel Bianchi, Oberursel (DE); Walter Pieter Hendrik Laurentius Van Der Klugt, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 475 days.

(21) Appl. No.: 17/940,072

(22) Filed: Sep. 8, 2022

(65) Prior Publication Data

US 2023/0081148 A1   Mar. 16, 2023

(30) Foreign Application Priority Data

Sep. 10, 2021 (EP) ..................... 21196063

(51) Int. Cl.
| | | |
|---|---|---|
| *A61F 13/15* | (2006.01) | |
| *A61F 13/515* | (2006.01) | |
| *A61F 13/534* | (2006.01) | |
| *A61F 13/58* | (2006.01) | |
| *A61F 13/53* | (2006.01) | |

(52) U.S. Cl.
CPC .......... *A61F 13/534* (2013.01); *A61F 13/515* (2013.01); *A61F 13/58* (2013.01); *A61F 2013/15373* (2013.01); *A61F 2013/15406* (2013.01); *A61F 2013/5307* (2013.01); *A61F 2013/53445* (2013.01)

(58) Field of Classification Search
CPC ...... A61F 13/534; A61F 13/515; A61F 13/58; A61F 2013/15406; A61F 2013/5307; A61F 2013/53445

See application file for complete search history.

(56) References Cited

U.S. PATENT DOCUMENTS

| | | |
|---|---|---|
| 3,799,167 A | 3/1974 | Miller et al. |
| 4,257,418 A | 3/1981 | Hessner |
| 4,315,508 A | 2/1982 | Bolick |
| 4,661,102 A | 4/1987 | Shikata |

(Continued)

FOREIGN PATENT DOCUMENTS

| | | |
|---|---|---|
| CN | 201930143 U | 8/2011 |
| CN | 202027809 | 11/2011 |

(Continued)

OTHER PUBLICATIONS

"Beary Small", Bili-Burns Phototherapy Diapers, 2015, Retrieved from : http://www.srnall-beginnings.com/#!blank/copk.

(Continued)

*Primary Examiner* — Jacqueline F Stephens
(74) *Attorney, Agent, or Firm* — Daniel S. Albrecht

(57) ABSTRACT

An absorbent article comprises a liquid-permeable topsheet, a liquid-impermeable backsheet, an absorbent core and a cushion layer between the absorbent core and the backsheet. The cushion layer comprises at least two sub-layers. The sub-layers advantageously have different widths or are bonded to each other by one or more longitudinally-extending attachment areas.

16 Claims, 10 Drawing Sheets

(56) References Cited

U.S. PATENT DOCUMENTS

| | | | |
|---|---|---|---|
| 4,950,264 A * | 8/1990 | Osborn, III | A61F 13/53747 604/385.08 |
| 5,026,364 A | 6/1991 | Robertson | |
| 5,383,871 A | 1/1995 | Carlin | |
| 5,386,595 A | 2/1995 | Kuen | |
| H1440 H | 5/1995 | New | |
| 5,653,842 A | 8/1997 | Kuen | |
| 5,702,377 A | 12/1997 | Collier, IV | |
| 5,707,364 A | 1/1998 | Coates | |
| 5,827,259 A | 10/1998 | Laux | |
| 5,843,066 A | 12/1998 | Dobrin | |
| 5,906,604 A | 5/1999 | Roennberg | |
| 5,931,827 A | 8/1999 | Buell | |
| 5,934,470 A | 8/1999 | Bauer et al. | |
| 5,938,652 A | 8/1999 | Sauer | |
| 5,941,863 A | 8/1999 | Guidotti | |
| 5,971,970 A | 10/1999 | Carlbark | |
| 5,993,433 A | 11/1999 | St Louis | |
| 6,010,490 A | 1/2000 | Freeland et al. | |
| 6,010,491 A | 1/2000 | Roe | |
| 6,120,486 A | 9/2000 | Toyoda | |
| 6,132,410 A | 10/2000 | Gompel | |
| 6,135,988 A | 10/2000 | Turner | |
| 6,142,985 A | 11/2000 | Feist | |
| 6,217,563 B1 | 4/2001 | Gompel | |
| 6,315,764 B1 | 11/2001 | Faulks | |
| 6,336,922 B1 | 1/2002 | Vangompel | |
| 6,371,950 B1 | 4/2002 | Roslansky | |
| 6,432,099 B2 | 8/2002 | Roennberg | |
| 6,491,677 B1 | 12/2002 | Glaug | |
| 6,626,880 B2 | 9/2003 | Onishi | |
| 6,627,786 B2 | 9/2003 | Roe | |
| 6,638,262 B2 | 10/2003 | Suzuki | |
| 6,659,993 B2 | 12/2003 | Minato | |
| 6,767,344 B2 | 7/2004 | Suzuki | |
| 6,772,708 B2 | 8/2004 | Klofta | |
| 6,790,203 B2 | 9/2004 | Een | |
| 6,817,993 B1 | 11/2004 | Simmons | |
| 6,921,394 B2 | 7/2005 | Sayama | |
| 6,926,702 B1 | 8/2005 | Wilkinson | |
| 7,118,557 B2 | 10/2006 | Minato | |
| 7,163,530 B1 | 1/2007 | Toyoshima | |
| 7,361,167 B2 | 4/2008 | Erickson et al. | |
| 7,419,562 B2 | 9/2008 | Van Gompel | |
| 7,753,899 B2 | 7/2010 | Mori | |
| 7,785,309 B2 | 8/2010 | Van Gompel | |
| 7,879,017 B1 | 2/2011 | Tabata | |
| 8,092,439 B2 | 1/2012 | Stabelfeldt et al. | |
| 8,181,278 B2 | 5/2012 | Odorzynski | |
| 8,216,201 B2 | 7/2012 | Beck | |
| 8,231,592 B2 | 7/2012 | Suzuki | |
| 8,430,858 B2 | 4/2013 | Baeck | |
| 8,449,518 B2 | 5/2013 | Allison-rogers | |
| 8,668,680 B2 | 3/2014 | Ichikawa | |
| 8,747,380 B2 | 6/2014 | Coates | |
| 8,764,721 B2 | 7/2014 | Van Gompel | |
| 8,764,722 B2 | 7/2014 | Rhein | |
| 8,821,467 B1 | 9/2014 | Minella | |
| 8,894,626 B2 | 11/2014 | Beck | |
| 8,926,580 B2 | 1/2015 | Carney | |
| 8,992,496 B2 | 3/2015 | Bäck | |
| 9,044,358 B2 | 6/2015 | Nakajima | |
| 9,168,181 B2 | 10/2015 | Popp | |
| 9,259,362 B2 | 2/2016 | Popp | |
| 9,445,951 B2 | 9/2016 | Moberg-alehammar | |
| 9,554,952 B2 | 1/2017 | Rönnberg | |
| 9,675,503 B2 | 6/2017 | Carney | |
| 2002/0016579 A1 | 2/2002 | Stenberg | |
| 2002/0072727 A1 | 6/2002 | Mishima et al. | |
| 2002/0111596 A1 | 8/2002 | Fletcher | |
| 2002/0120248 A1 | 8/2002 | Onishi | |
| 2002/0138054 A1 | 9/2002 | Erdman | |
| 2003/0050616 A1 | 3/2003 | Reynolds | |
| 2003/0124928 A1 | 7/2003 | Sherrod | |
| 2003/0232556 A1 | 12/2003 | Toro | |
| 2004/0102757 A1 | 5/2004 | Olson | |
| 2004/0127867 A1 | 7/2004 | Odorzynski et al. | |
| 2004/0158212 A1 | 8/2004 | Ponomarenko | |
| 2004/0230171 A1 | 11/2004 | Ando | |
| 2005/0222546 A1 | 10/2005 | Vargo | |
| 2006/0247597 A1 | 11/2006 | Hogan | |
| 2007/0049895 A1 | 3/2007 | Van Gompel | |
| 2007/0102750 A1 | 5/2007 | Kim | |
| 2007/0232180 A1 | 10/2007 | Polat | |
| 2007/0233027 A1 | 10/2007 | Roe et al. | |
| 2008/0065034 A1 | 3/2008 | Vargo | |
| 2008/0082072 A1 | 4/2008 | Helmfridsson | |
| 2010/0004616 A1 | 1/2010 | Nakamura et al. | |
| 2010/0168695 A1 | 7/2010 | Robles | |
| 2010/0234822 A1 | 9/2010 | Baeck | |
| 2010/0241098 A1 | 9/2010 | Brownlee | |
| 2011/0184372 A1 | 7/2011 | Esping | |
| 2012/0116339 A1 | 5/2012 | Labit et al. | |
| 2012/0177886 A1 | 7/2012 | Kanya | |
| 2013/0110065 A1 | 5/2013 | Takahashi et al. | |
| 2014/0068839 A1 | 3/2014 | Steele et al. | |
| 2014/0107605 A1 | 4/2014 | Schroer, Jr. | |
| 2014/0135724 A1 | 5/2014 | Robles et al. | |
| 2014/0142528 A1 | 5/2014 | Wang et al. | |
| 2014/0142529 A1 | 5/2014 | Cheng | |
| 2014/0155856 A1 | 6/2014 | Ronnberg et al. | |
| 2014/0163501 A1 | 6/2014 | Ehrnsperger et al. | |
| 2014/0221956 A1 | 8/2014 | Martynus et al. | |
| 2014/0257227 A1 | 9/2014 | Roe | |
| 2014/0303589 A1 | 10/2014 | Paz et al. | |
| 2014/0345034 A1 | 11/2014 | Hansson et al. | |
| 2014/0350508 A1 | 11/2014 | Popp | |
| 2014/0375297 A1 | 12/2014 | Geiger et al. | |
| 2015/0065973 A1 | 3/2015 | Roe et al. | |
| 2015/0088086 A1 | 3/2015 | Beck | |
| 2015/0265475 A1 | 9/2015 | Joseph et al. | |
| 2015/0282997 A1 | 10/2015 | Arizti | |
| 2017/0246043 A1 | 8/2017 | Ludwig | |
| 2017/0246044 A1 | 8/2017 | Ludwig | |
| 2017/0246052 A1 | 8/2017 | Ludwig | |
| 2017/0246053 A1 | 8/2017 | Ludwig et al. | |
| 2019/0060130 A1 | 2/2019 | Tally et al. | |
| 2019/0105206 A1 | 4/2019 | Ludwig et al. | |
| 2019/0336343 A1 | 11/2019 | Etchells et al. | |
| 2019/0374397 A1 * | 12/2019 | Tally | A61F 13/493 |
| 2020/0179190 A1 | 6/2020 | Johnston et al. | |
| 2021/0177669 A1 | 6/2021 | Peri et al. | |
| 2021/0401637 A1 | 12/2021 | Tally et al. | |

FOREIGN PATENT DOCUMENTS

| | | |
|---|---|---|
| CN | 202191413 | 2/2012 |
| CN | 202207245 | 5/2012 |
| CN | 202288655 | 7/2012 |
| CN | 102011007821 | 10/2012 |
| CN | 202515884 | 11/2012 |
| CN | 202801952 | 3/2013 |
| CN | 102217995 | 6/2013 |
| CN | 203107440 U | 8/2013 |
| CN | 203576766 U | 5/2014 |
| CN | 204709180 | 10/2015 |
| CN | 204932009 | 1/2016 |
| CN | 106726167 | 5/2017 |
| CN | 206342616 | 7/2017 |
| CN | 206777460 U | 12/2017 |
| CN | 107714307 A | 2/2018 |
| DE | 3810473 A1 | 10/1989 |
| DE | 102011007818 | 10/2012 |
| EP | 2813201 A1 | 12/2014 |
| EP | 2901991 A1 | 8/2015 |
| GB | 2080093 B | 12/1984 |
| JP | S62199803 A | 9/1987 |
| JP | 2004195083 A | 7/2004 |
| JP | 2003175066 A5 | 7/2005 |
| JP | 2005304605 A | 11/2005 |
| JP | 2009082484 A | 4/2009 |
| JP | 2011072657 A | 4/2011 |
| JP | 2011072659 A | 4/2011 |
| JP | 2011098032 A | 5/2011 |

(56) References Cited

FOREIGN PATENT DOCUMENTS

| | | | |
|---|---|---|---|
| JP | 2011136063 A | 7/2011 | |
| JP | 2012010904 A | 1/2012 | |
| JP | 2013530758 A | 8/2013 | |
| JP | 2013255841 A | 12/2013 | |
| JP | 5690966 B1 | 2/2015 | |
| JP | 2015037591 A | 2/2015 | |
| JP | 2015188715 A | 11/2015 | |
| JP | 2015223257 A | 12/2015 | |
| JP | 2016030200 A | 3/2016 | |
| JP | 2016030201 A | 3/2016 | |
| JP | 2016030202 A | 3/2016 | |
| JP | 5934815 B1 | 5/2016 | |
| JP | 3205471 B2 | 7/2016 | |
| JP | 2019118587 A | 7/2019 | |
| TW | 201626969 A | 8/2016 | |
| WO | WO-0019955 A2 * | 4/2000 | ......... A61F 13/4751 |
| WO | 0101907 A1 | 1/2001 | |
| WO | 03082167 A2 | 10/2003 | |
| WO | 2010020990 A3 | 5/2010 | |
| WO | 2012143227 A1 | 10/2012 | |
| WO | 2012143228 A1 | 10/2012 | |
| WO | 2012143230 A1 | 10/2012 | |
| WO | 2012145964 A1 | 11/2012 | |
| WO | 2015046632 A1 | 4/2015 | |
| WO | 2016013258 A1 | 1/2016 | |
| WO | 2016013662 A1 | 1/2016 | |
| WO | 2016013663 A1 | 1/2016 | |
| WO | 2016104148 A1 | 6/2016 | |
| WO | 2016121183 A1 | 8/2016 | |
| WO | 2016121236 A1 | 8/2016 | |

OTHER PUBLICATIONS

All Office Actions, U.S. Appl. No. 16/432,969, filed Jun. 6, 2019.
All Office Actions, U.S. Appl. No. 17/471,305, filed Sep. 10, 2021.
Andrea Brown, "8 Tips for Sewing the Smoothest Curved Seams", Retrieved from: https://www.craftsy.com/post/sewing-curved-seams/#, Sep. 29, 2021.
Extended EP Search Report and Written Opinion for 21196063.8 dated Feb. 10, 2022, 09 pages.
PCT Search Report and Written Opinion for PCT/US2022/076018 dated Dec. 16, 2022, 13 pages.

* cited by examiner

ABSORBENT ARTICLE COMPRISING A MULTI-LAYER CUSHION LAYER

CROSS-REFERENCE TO RELATED APPLICATION

This application claims the benefit, under 35 U.S.C. § 119(a), of European Patent Application No. 21196063.8, filed on Sep. 10, 2021, which is herein incorporated by reference in its entirety.

FIELD

The invention relates to absorbent articles for personal hygiene, such as baby diapers and adult incontinence products. The absorbent articles comprise a cushion layer disposed between the absorbent core and the backsheet.

BACKGROUND

Personal absorbent hygiene articles such as diapers are used to keep babies, young children or incontinent adults from soiling their beds or clothes. Continuous improvements over the years have led to diapers that are today comfortable to use and highly efficient at preventing leakages. An absorbent core within the article comprises an absorbent material that absorbs and stores the body fluids. While superabsorbent polymers (SAP) mixed with cellulose fibers are widely used in the industry as absorbent material, there is a trend to reduce or even remove absorbent pulp fibers from the absorbent core.

One drawback of cores comprising a high proportion of SAP and little or no cellulose fibers is that a caregiver may feel individual superabsorbent particles through the backsheet. This may be unfavorably perceived by the user as a gritty feeling. US2019/0374397A1 discloses using a masking material positioned at least partially intermediate the absorbent core and the backsheet to avoid this gritty feeling. The masking material still has a low enough stiffness to allow the absorbent article to remain flexible and conform to the wearer.

There is a continuous need for absorbent articles combining high absorbency properties and softness.

SUMMARY

The present invention is for a personal hygiene absorbent article. The absorbent article comprises a liquid-permeable topsheet, a liquid-impermeable backsheet, an absorbent core comprising an absorbent material between the topsheet and the backsheet, and a cushion layer disposed between the absorbent core and the backsheet. The absorbent material comprises at least 50% by weight superabsorbent polymers, optionally mixed with cellulose fibers. According to the invention, the cushion layer comprises at least two sub-layers. The sub-layers may be stacked individual layers, or the sub-layers may be formed by folding a layer of cushion layer material, the folds forming the sub-layers.

In a first aspect, the sub-layers are arranged so that the cushion layer has a higher basis weight in a longitudinally-extending central area relative to the lateral areas disposed transversally outwardly of this central area. In this manner, the cushion layer provides increased cushiness in this central area of the article, where it is most needed. This can be obtained by providing at least two sub-layers with different width.

In a second aspect, at least two vertically adjacent sub-layers forming the cushion layer are attached to another at their interface along a central longitudinally-extending attachment area but are not attached to another along lateral non-attachment areas disposed transversally outwardly of the central attachment area. This provides for better flexibility of the cushion layer, especially when submitted to lateral compression.

In a third aspect, the cushion layer and the lower substrate layer of the core wrap are only partially bonded to each other at their interface, in particular wherein the bonded portion comprises a longitudinally-extending bonded portion and optionally one or more corner bonded portion(s) or one or more transversal bonded edge portion(s).

Any of the aspects may of course be combined with any of the other, for example the first aspect may be combined with the second aspect, the second aspect with the third aspect, and/or the first, second and third aspects may be combined in an absorbent article.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION

Definitions

Figure 1:
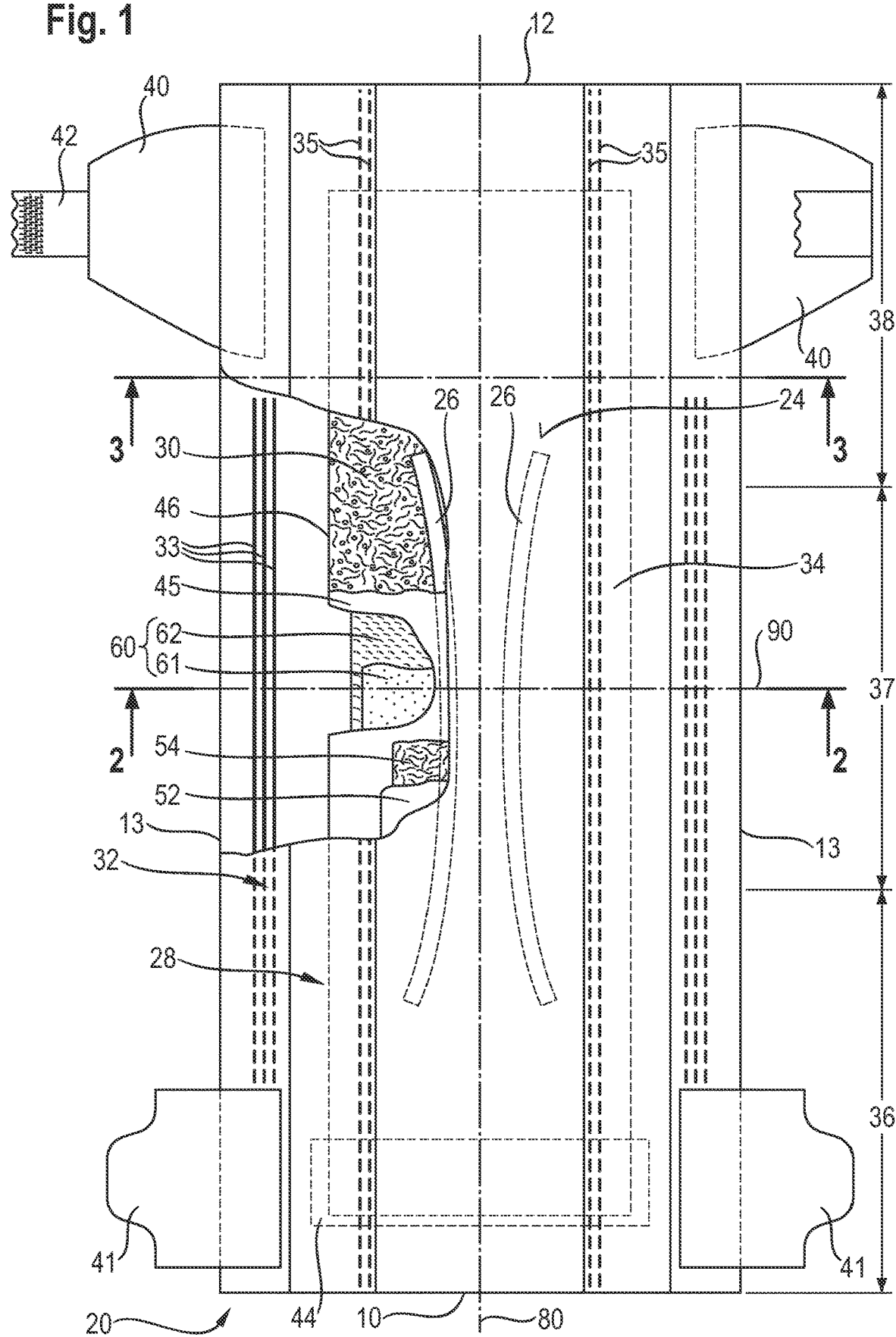
FIG. 1 is a top view from an exemplary absorbent article in the form of a taped diaper with some layers partially removed.

As used herein, "absorbent articles" refers to devices that are placed against or in proximity to the body of the wearer to absorb and contain the various exudates discharged from the body. Absorbent articles include diapers (baby and infant diapers as well as diapers for adult incontinence), absorbent inserts (which are intended to be inserted into an outer cover to form a diaper or pant), feminine care absorbent articles (such as sanitary napkins and pantiliners), and the like. The present invention is particularly suitable to be used in absorbent articles in the form of disposable taped diapers and disposable pant diapers. As used herein, the term "exudates" includes, but is not limited to, urine, blood, vaginal discharges, sweat and fecal matter.

As used herein, "diaper" refers to an absorbent article generally worn by babies, infants and incontinent adults about the lower torso so as to encircle the waist and legs of the wearer and that is specifically adapted to receive and contain urinary and fecal waste. Diapers can be generally characterized as taped diapers or pant diapers. In a taped diaper, the back half of the diaper can be releasably attached to the front half by a tape system. In a pant diaper, the waist opening and the leg openings are pre-formed by a left seam and right seam at the edge of the diaper pant. With diaper pants, the caretaker (or the wearer itself if able to do so) inserts the wearer's feet and legs into the leg openings and then slide the pant diaper up into position about the wearer's lower torso. A pant diaper may be pre-formed by any suitable technique including, but not limited to, joining together portions of the absorbent article using re-fastenable and/or non-refastenable bonds (e.g., seam, weld, adhesive, cohesive bond, fastener, etc.). A pant diaper may be pre-formed anywhere along the circumference of the article (e.g., side fastened, front waist fastened).

As used herein, the terms "nonwoven", "nonwoven web" and "nonwoven layer" are used interchangeably. Nonwovens are broadly defined as engineered fibrous assemblies, primarily planar, which have been given a designed level of structural integrity by physical and/or chemical means, excluding weaving, knitting or paper making. The fibers may be of natural origin, such as cotton or bamboo fibers, or man-made origin. Synthetic fibers may be selected from the group consisting of polyolefins (such as polyethylene, polypropylene or combinations and mixtures thereof), polyethylene terephthalate (PET), co PET, polylactic acid (PLA), polyhydroxy alkanoid (PHA), or mixtures or combinations thereof. The fibers may be staple fibers (e.g. in carded nonwoven webs/layers) or continuous fibers (e.g. in spunbonded or meltblown nonwoven webs/layers).

Nonwoven webs/layers can be formed by many processes such as meltblowing, spunlaying, solvent spinning, electrospinning, and carding, and the fibers can be consolidated, e.g. by hydroentanglement (in spunlaced nonwoven webs/layers), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify. The basis weight of nonwoven fabrics is usually expressed in grams per square meter ($g/m^2$).

Nonwoven materials can be formed by a variety of fiber materials (PP, PE, PET, coPET, bicomponent, and mixture thereof) and, in some cases, the fibers or the nonwovens can be treated to enhance specific fluid handling characteristics, such as fluid permeability or fluid barrier properties.

The term "dtex" as used herein refers to a unit used to indicate the fineness of a filament/fiber. The unit expresses the mass of a filament/fiber in grams per 10,000 meters of length.

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Longitudinal" refers to a direction running perpendicular from the middle of a waist edge to the middle of an opposing waist edge of the article, notionally defined a longitudinal centerline. Absorbent articles are symmetrically constructed relative to this longitudinal centerline. "Transverse" refers to a direction perpendicular to the longitudinal direction. As used herein, "longitudinally-extending" refers to a feature of the article extending at least twice as much in the longitudinal direction than in the transversal direction.

"Body-facing" and "garment-facing" refer respectively to the relative location of an element or a surface of an element or group of elements. "Body-facing" implies the element or surface is nearer to the wearer during wear than another element of the same component. "Garment-facing" implies the element or surface is more remote from the wearer during wear than another element of the same component. The garment-facing surface may face another garment of the wearer, or other items, such as the bedding, or the atmosphere.

General Description of an Exemplary Diaper 20

FIG. 1 is a plan view of an exemplary taped diaper 20, in a flat-out state, with portions of the diaper being cut-away to more clearly show the construction of the diaper. This diaper 20 is shown for illustration purpose only. The structure of the present invention may be used in a wide variety of other absorbent articles, for example absorbent diaper pants having pre-formed side seams. The side seams of pant articles can be opened by cutting or otherwise, if it is desired to place the pant in a flattened out configuration.

Figure 2:
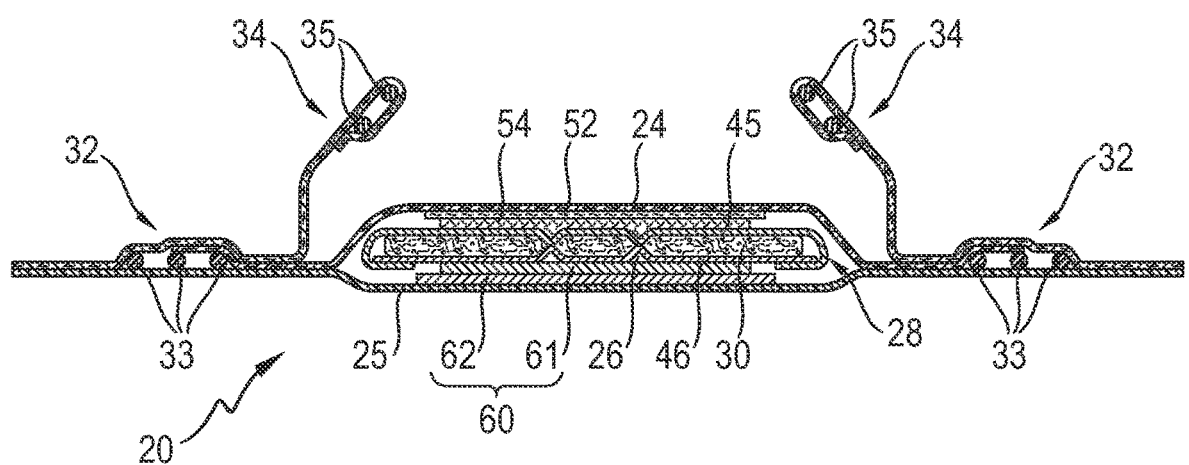
FIG. 2 is a schematic cross-section view of FIG. 1 along line 2-2.

As illustrated in FIG. 1-2, the absorbent article comprises a topsheet 24, backsheet 25, and an absorbent core 28 which is positioned between the topsheet 24 and the backsheet 25. The absorbent core 28 comprises an absorbent material 30, having a deposition area having a pre-determined shape in the plane formed by the article when flattened-out. The shape of the deposition area of the absorbent material 30 may be substantially rectangular as illustrated in FIG. 1, or have another shape such as a tapered outline as in a sand-hour shape. The absorbent core 28 may optionally comprise longitudinally-extending channels 26, which are areas substantially free of absorbent material, to facilitate the distribution of a fluid along the length of the absorbent article. When discussing the vertical position of an element of the article, "up" or "top" refers to an orientation or direction closer to the topsheet, and "down" or "bottom" to an orientation or direction closer the backsheet.

Absorbent articles, such as the diaper 20 illustrated in FIGS. 1-2, typically comprise an acquisition layer 52 directly underneath the topsheet. The acquisition layer may for example be a surfactant-treated, latex-bonded nonwoven acquisition layer. A distribution layer 54 may be further optionally present between the acquisition layer and the absorbent core. The distribution layer 54 may for example consist of cross-linked cellulose fibers. The prior art discloses many types of acquisition-distribution layers, see for example WO2000/59430, WO95/10996, U.S. Pat. No. 5,700,254, WO02/067809.

The absorbent article 20 may also comprise inner barrier leg cuffs 32 and outer leg cuffs 34. The inner barrier cuffs 34 can extend upwards from the surface of the article to provide retention of the waste, while the outer cuffs 33 are typically formed in the plane of the chassis of the article as defined by topsheet and backsheet, as is known in the art. These cuffs are preferably elasticized, as is known in the art, for example using elastic threads 33, 35 as represented in the Figures. Moreover, the absorbent article may comprise a fastening system, such as an adhesive fastening system or a hook and loop fastening member, which can comprise tape tabs 42 disposed on back ears 40, such as adhesive tape tabs or tape tabs comprising hook elements, cooperating with a landing zone 44 (e.g. a nonwoven web providing loops in a hook and loop fastening system). While taped diapers typically comprise back ears 40, and front ears 46, these are typically not present in pant-type absorbent articles having pre-formed side seams.

The front ears 41 and/or back ears 40 may be discrete components attached to the chassis of the absorbent article or may instead be continuous with portions of the topsheet and/or backsheet such that these portions form all or a part of the front and/or back ears 41, 40. Also combinations of the aforementioned are possible, such that the front and/or back ears are formed by portions of the topsheet and/or backsheet while additional materials are attached to form the overall front and/or back ears. The front and/or back ears may be elastic or non-elastic. Also, the front ears 40 may be applied as separate components attached to the absorbent article while the back ears (or parts thereof) 46 may be continuous with portions of the backsheet and/or topsheet—or vice versa.

The absorbent article, whether taped or pant diaper, can be notionally divided in a front waist region 36 (which is oriented towards the belly of the wearer in use), a back waist region 38 (which is oriented towards the back of the wearer) opposed to the front waist region 36 and a crotch region 37 located between the front waist region 36 and the back waist region 38. The crotch region, the front waist region and back waist region each represents one third of the absorbent article as measured along the longitudinal centerline 80. The longitudinal centerline 80 is the imaginary line dividing the article along its length in two equal halves. The transversal centerline 90 is the imagery line perpendicular to the longitudinal centerline 80 in the plane of the flattened-out diaper and going through the middle of the length of the article. The periphery of the diaper 20 is defined by the outer edges of the diaper. Both longitudinal edges 13 may run generally parallel to the longitudinal centerline 80 of the diaper 20, and the front waist edge 10 and the back waist edge 12 typically join the longitudinal edges and are generally parallel to the transversal centerline 90 of the article 20.

Further, the absorbent article may comprise other optional but conventional elements, which are not represented for simplicity, such as an elastic back waist feature, a front waist elastic feature, a lotion applied onto the body-facing surface of the topsheet, or a urine indicator disposed on the inner side of the backsheet that changes color when contacted with urine.

The topsheet 24, the backsheet 25, the absorbent core 28 and other components of the articles may be assembled in a variety of well-known configurations, in particular by gluing, heat embossing, ultrasonic bonding or combinations thereof, unless indicated otherwise. Exemplary diaper configurations are described generally in U.S. Pat. Nos. 3,860,003; 5,221,274; 5,554,145; 5,569,234; 5,580,411; and 6,004,306.

The topsheet 24 is the part of the absorbent article 20 that is in contact with the wearer's skin. At least a portion of, or all of, the topsheet is liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polypropylene or bicomponent PE/PP fibers or mixtures thereof), or a combination of natural and synthetic fibers. The topsheet may have one or more layers. The topsheet may be apertured or non-apertured, and may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 25 is generally that portion of the absorbent article 20 that constitutes all or a part of the garment-facing surface of the absorbent article. The backsheet 25 may be joined at least partially to the topsheet 24, the absorbent material 30, the substrate layer 46, or the cushion layer 60, by any attachment methods known to those of skill in the art. The backsheet 25 prevents, or at least inhibits, the bodily exudates absorbed and contained in the absorbent material 30 from soiling articles such as bedsheets, undergarments, and/or clothing. The backsheet is typically liquid impermeable, or at least substantially liquid impermeable.

The backsheet 25 is typically comprised of a thin impermeable plastic film, usually a thermoplastic film having a thickness of about 0.01 mm to about 0.05 mm. The backsheet material may be breathable, which permit vapors to escape from the absorbent article, while still preventing, or at least inhibiting, bodily exudates from passing through the backsheet. A breathable backsheet may have a Water Vapor Transmission Rate (WVTR) of from 1,000 to 15,000 $g/m^2/24$ h, or from 1,000 to 10,000 $g/m^2/24$ h, or from 1,500 to 10,000 $g/m^2/24$ h as measured using a PERMATRAN-W Model 101K (available from Mocon, Inc., Minneapolis, MN) or equivalent, according to Nonwovens Standard Procedure NWSP 70.4.R0(15) with the following specifications: experiments were carried out in a lab controlled at 23° C.±2 C.° and 50% RH±2% RH and the instrument cells heated to 37.8° C. (100° F.).

The backsheet 25 may also comprise a backsheet nonwoven outer cover (not represented). The backsheet nonwoven outer cover is typically a thin nonwoven material that is laminated to the outer surface of the backsheet film. The outer cover nonwoven may thus form the outermost garment-facing surface of the backsheet. The backsheet nonwoven outer cover may comprise a bond pattern, apertures, and/or three-dimensional features, and may improve the feel of the backsheet.

The wearer-facing side of the backsheet is typically applied with a broad adhesive coverage 75, which may be typically applied by spiral glue application, as is known in the art. This adhesive coverage 75 may be used to secure the cushion layer 60 to the backsheet 25.

The absorbent material 30 comprises at least 50% by weight of superabsorbent polymer particles, by weight of the absorbent material, and preferably more. Suitable superabsorbent polymer are any water-insoluble, water-swellable polymers capable of absorbing large quantities of fluids, as is known in the art. The term "superabsorbent polymer" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The superabsorbent polymer may in particular have a CRC value of more than 20 g/g, or more than 24 g/g, or of from 20 to 50 g/g, or from 20 to 40 g/g, or 24 to 35 g/g.

The absorbent material may further comprise at least 60 weight-%, or at least 70 weight-%, or at least 80 weight-% or at least 90 weight-% of superabsorbent polymer particles, by total weight of the absorbent material. The rest of the absorbent material may be cellulose fibers or synthetic fibers which are mixed with the superabsorbent polymer particles. The absorbent material may be completely free of cellulose fibers or at least comprises one layer of superabsorbent polymer particles which is free of cellulose fibers. Such absorbent cores without cellulose fibers are referred to in the art as airfelt free cores. The superabsorbent particles may in particular be immobilized by a microfibrous net of adhesive or thermoplastic polymer, or alternatively supported within a high loft, porous nonwoven, as is known in the art. In airfelt-free cores, the SAP particles may be enclosed in pockets, see for example U.S. Pat. No. 5,433,715 (Tanzer et al.), WO2012/052172 (Van Malderen), or is immobilized by a fibrous network of adhesive fibers (e.g. US2008/312617, Hundorf et al.), or immobilized within the pores of a high loft nonwoven (see e.g. WO2016/06021, Bianchi et al.).

The absorbent material 30 typically defines a deposition area, when considered in the plane of the absorbent article as shown in FIG. 1, having a pre-determined shape. The deposition area may have any shape, in particular a rectangular shape as illustrated in FIG. 1, but other shapes are common such as dog-bone or sand-hour shaped having a tapering in the crotch region of the article. The absorbent material 30 is disposed between an upper substrate layer 45 oriented towards the topsheet and a lower substrate layer 46 oriented towards the backsheet. These substrate layers sandwich the absorbent material and together form the absorbent core 28. The upper substrate and lower substrate layer are commonly referred together as core wrap. The upper and lower substrate layer 45, 46 may be any material capable of providing a support for the absorbent material. The substrate layers are typically made of a nonwoven web but other suitable materials are possible, such as paper. The substrate layers have a low basis weight, (typically less than 20 gsm, in particular less than 14 gsm). A preferred substrate material may be a SMS nonwoven (Spunbond-Meltblown-Spunbond laminate), as is known in the art. For those absorbent articles that do not require an upper acquisition-distribution layer or system 52, 54, then the upper substrate layer 45 can be provided directly between the topsheet 24 and the absorbent material 30.

The absorbent core may comprise a layer of adhesive 72, referred to as auxiliary glue, on the inner surface of the upper substrate and/or lower substrate facing the absorbent material 30. This adhesive may be typically applied by slot coating in a series of longitudinally-extending slots, as is known in the art. The adhesive further helps immobilizing the absorbent material within the core wrap. The auxiliary adhesive 72 may also serve to form a channel bonds between the upper and lower substrates, through the absorbent-material free channels 26.

The upper and the lower substrate layers 45, 46 may be made of two separate piece of material that are partially bonded to each other, e.g. in a C-wrap configuration, as illustrated in the Figures Alternatively the core wrap may be formed by a single piece of material that forms the upper and the lower substrate layers. The upper and lower substrate layers may be made of the same or different materials, i.e. two nonwoven webs which have the same of different properties. The substrate layers 45, 46 are preferably bonded longitudinally to prevent the absorbent material from being released sideways, for example using a longitudinal side adhesive 73. The substrate layers may also be optionally bonded transversally at the front and the back of the absorbent core. The substrate layers may be bonded face to face, at least longitudinally, but other bonding configurations are possible, in particular a C-wrap configuration where one of the top or bottom substrate layer is larger than the other, so that flaps can be folded around the absorbent material and attached to the other substrate, as illustrated in FIG. 2. Portions of the upper substrate layer 45 may be folded over the longitudinal edges of the layer of absorbent material, such that these portions are positioned on the garment-facing surface of the absorbent material. Alternatively, or in addition, portions at and adjacent to the longitudinal edges of the lower substrate layer 46 may be folded over the longitudinal edges of the layer of absorbent material, such that these portions are positioned on the body-facing surface of the absorbent material.

The absorbent core may optionally comprise one or more channel(s) 26, which are areas within the absorbent material that where substantially no absorbent material is present, apart possibly from accidental discrete contamination. The term "the channels" is used below to refer to "at least one or more channels" for simplicity. The channels preferably do not extend to any of the side of the absorbent core, and thus at least some of the channels are completely surrounded by the absorbent material. The channels are typically elongated in the longitudinal direction. The channels may have a length of from 10% and 80%, or from 20% to 70%, or from 30% to 60%, of the longitudinal dimension of the absorbent article (as measured along the longitudinal centerline 80). The channel may be straight, curved, or combinations thereof. The channels are typically symmetrically disposed relative to the longitudinal axis, and may be disconnected from another, as illustrated in FIG. 1, alternatively the channels may be connected at one or both their extremities to form a U or O shape. Such channels are disclosed in further details e.g. in WO2012170778A1, WO2012170781 (Kreuzer et al). The absorbent core may comprise one or more of channels which is/are at least partially present in the crotch region 37 of the article 20, optionally extending into the front and back waist regions 36, 38, or extending only to the front waist region or the back waist region. Any channel shapes are possible, for example a pair of longitudinally-extending central channels may also be joined at their extremities to form a generally U or O shape.

The upper substrate layer 45 and lower substrate layer 46 of the absorbent core may be bonded to each other through at least a portion of the length of the channels. This channel bond provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive 72 may be for example applied in the areas of the channels on the inner side of the upper substrate side and/or the inner side of the lower substrate of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO2012/170798A1 (Jackels et al.), EP2,905,000 (Jackels et al.) and EP2,905,001 (Armstrong-Ostle et al.).

Other bonding such as thermo bonding, mechanical bonding, ultrasonic bonding can also be used as additional bonding or as an alternative bonding. For example, an adhesive bonding may be reinforced by a thermo bonding, mechanical bonding or ultra-sonic bonding. Such thermo, mechanical or ultrasonic bonding can be applied on the channels through the external sides of the core wrap substrates.

Typically, the bonds may generally have the same outline and shape as the channels 26 in which they are contained, but may be slightly smaller to allow for a safety margin (e.g. by a few mm) as some deviations from the optimal registration may happen during high speed process. The channels may also be not bonded, or have one or more section which is bonded and one or more section that is not bonded.

Cushion Layer 60

As indicated above, the absorbent material 30 has a relatively high proportion of superabsorbent polymer particles. The resulting layer of absorbent material 30 has a reduced thickness in the dry state compared to conventional absorbent cores including higher amount of cellulosic fibers. The reduced thickness helps to improve the fit and comfort of the absorbent article for the wearer. However, since the superabsorbent particles are mixed with little or even no cellulose fibers, the superabsorbent particles may feel hard and gritty to the touch through the through the backsheet, on the wearer-facing side the article.

In order to address this problem, a cushion layer 60 is disposed between the absorbent core 28 and the backsheet 25. The cushion layer 60 provides a separation between the SAP particles and the garment-facing side of the absorbent article. The cushion layer 60 advantageously has a sufficient thickness and basis weight in order to provide for this function. While it would be desirable that the cushion layer extends transversally and longitudinally to have the same dimension as absorbent core, this represents a substantial material cost upcharge. Furthermore, such a large cushion layer may reduce the flexibility of the article.

According to the present invention, it was found that the cushion layer 60 advantageously comprises at least two sub-layers. The sub-layers may be provided by stacking discrete sub-layers 61, 62, or by folding a cushion layer material, in which case each the sub-layer(s) is/are formed by one or more folds of the cushion layer material. This will be further illustrated in the examples below and accompanying Figures explaining different aspects of the invention.

First Aspect of the Invention

According to a first aspect of the invention, this multi-layer construction of the cushion layer allows for optimization of the basis weight allowing to stack sub-layers of different width creating more caliper in a central area of the article. It was found that the center of the article is the area where cushioning is most needed, because typically the concentration of the SAP is higher in that region, and also because softness is often assessed in the center of the article rather than on the lateral or longitudinal sides. It was thus found that it is advantageous to provide more cushion material in the center of the article.

Figure 3A:
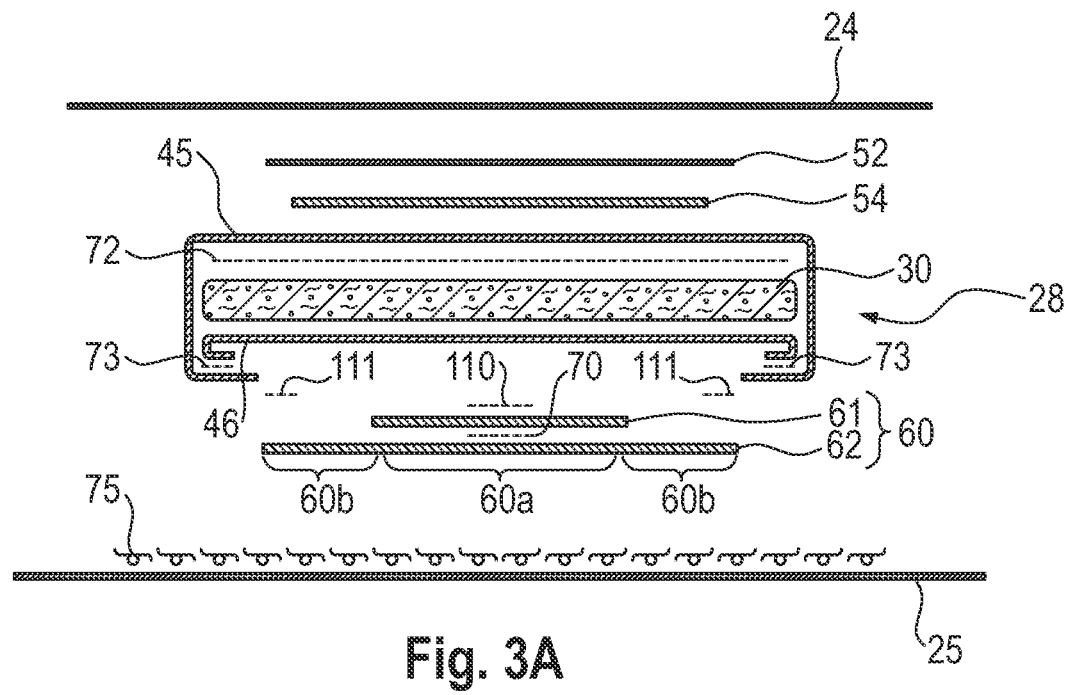
FIG. 3A is a schematic exploded cross-section view of FIG. 1 along line 3-3.

Accordingly, in this first aspect of the invention, the cushion layer comprises at least one first sub-layer having a smaller width than a second sub-layer. A simple execution of the first aspect is illustrated in FIG. 3A, where a first sub-layer 61 is stacked on top of a larger sub-layer 62. The first sub-layer 61 and second sub-layer 62 form the cushion layer 60. The sub-layers are aligned with the longitudinal axis so that they are symmetrically disposed relative to the longitudinal centerline, as shown in the Figures.

By providing two sub-layers of different widths, a cushion layer 60 comprising a higher basis weight central area 60a corresponding to the width of the narrower sub-layer 61 is provided. The two lateral areas 60b disposed transversally outwardly of the central area 60a have a lower basis weight than the central area 60a. This construction has the advantage of being economical in material, as less cushion material is used for the lateral sides of the cushion layer. Also, the flexibility of the article is improved on the lateral sides of the article due to the lower basis weight of the cushion layer in the lateral areas.

The sub-layers are advantageously made of the same cushion material. The different sub-layers also advantageously have the same length (measured along the longitudinal centerline 80), which may be about the length of the absorbent core, or may be smaller than the length of the absorbent core. The length of the sub-layers may be comprised in the range of from 40% to 100% of the length of the absorbent core, for example from 50% to 90% of the length of the absorbent core.

Having sub-layers of the same length simplifies the construction of the article. A single web of cushion material can be divided in several sub-layers by continuously slitting the single web in the longitudinal direction to forms the sub-layer web, then transversally cutting these and stacking these to form the cushion layer.

Figure 13:
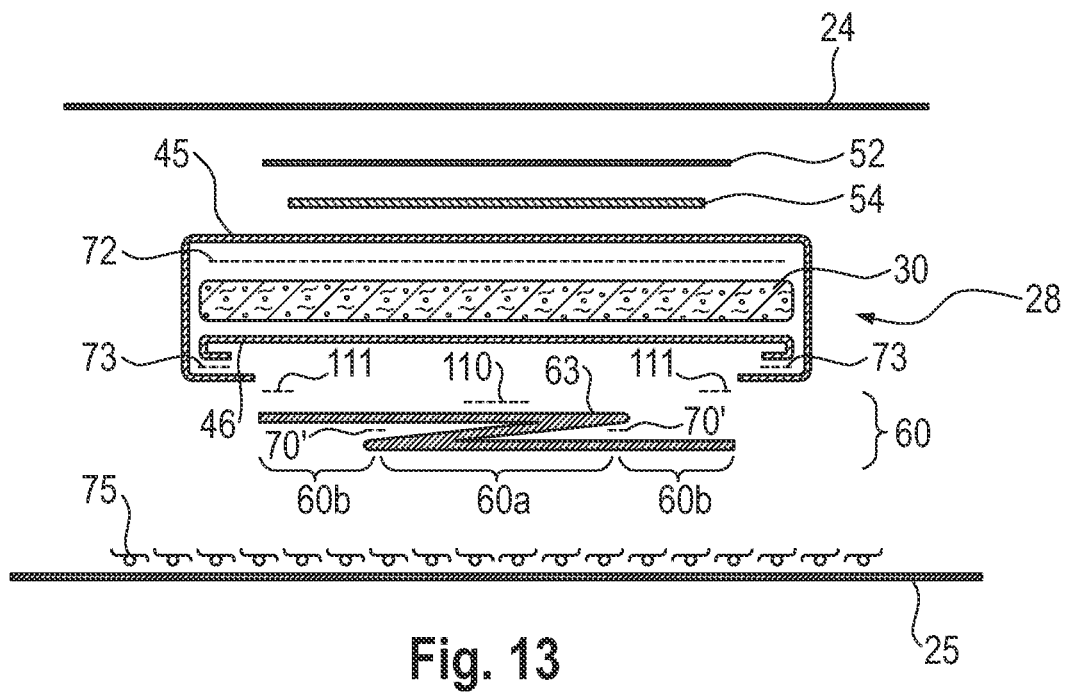
FIGS. 13-14 show alternative Z-folded multi-layer constructions.
Figure 14:
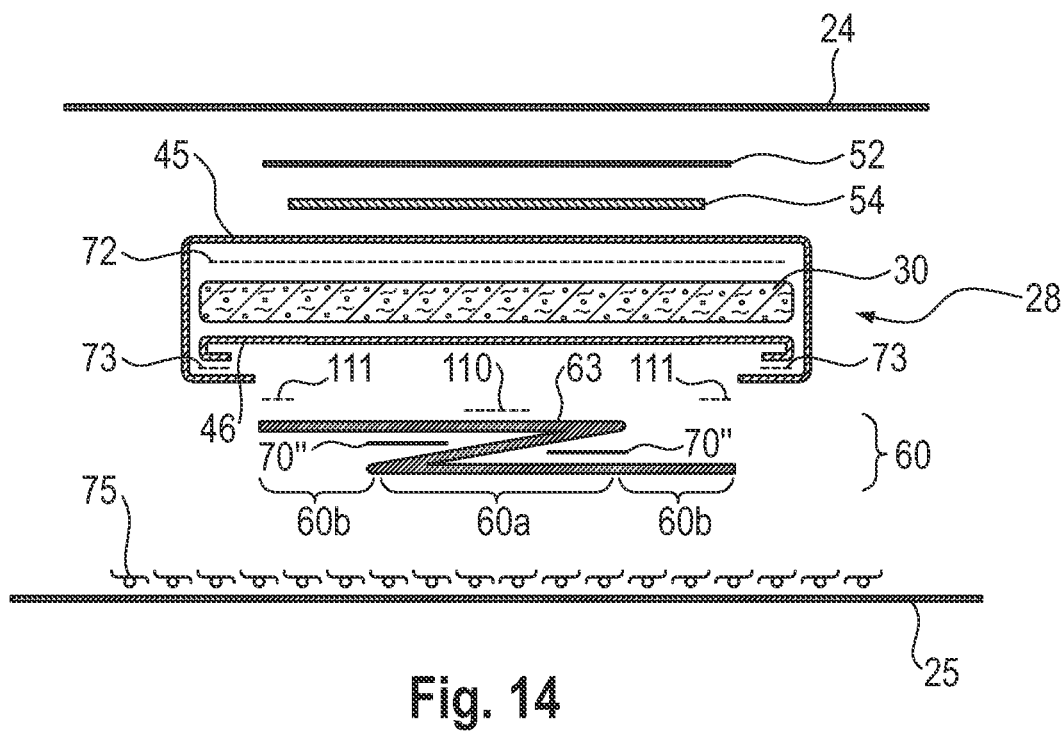
Figure 15:
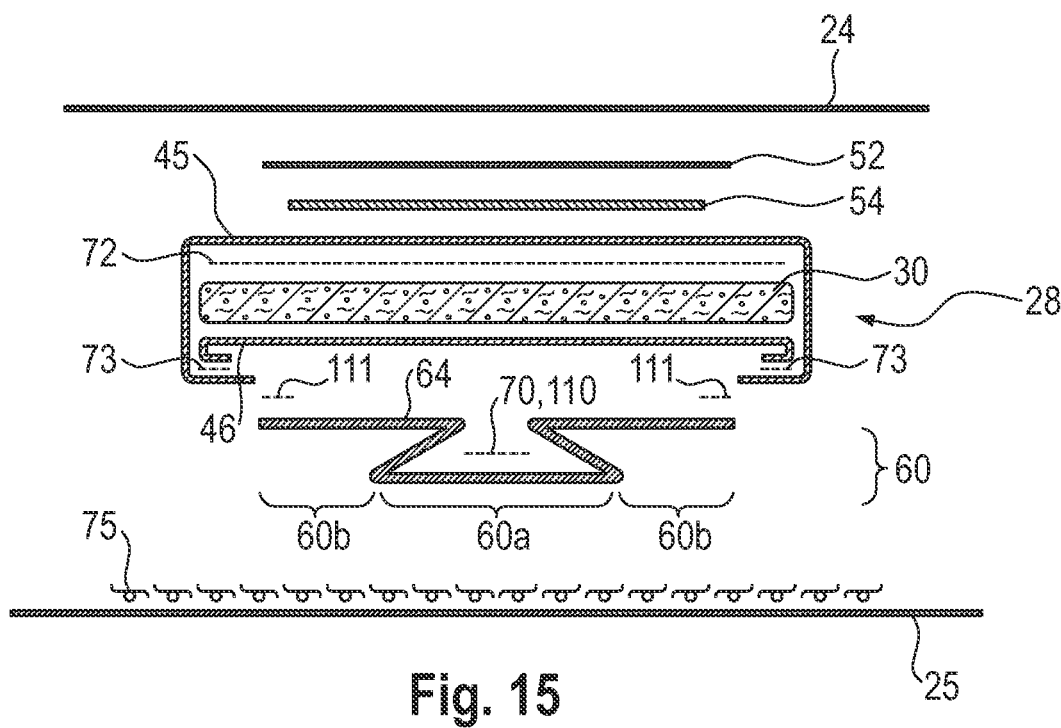
FIG. 15 shows an alternative Omega-folded multi-layer construction.

As an alternative to stacking discrete sub-layers, the original single web of cushion material may be folded to accomplish a similar cushion layer construction having areas of the different basis weight (as exemplified in FIGS. 13-15). The cushion material may be provided on a converting line as a roll of material that is unwound during manufacture, as is known in the art. Using a single roll to make the sub-layers provides a more stable process (the larger the roll is the more stable it is) while providing a longer runtime before the roll needs to be replaced.

Figure 4A:
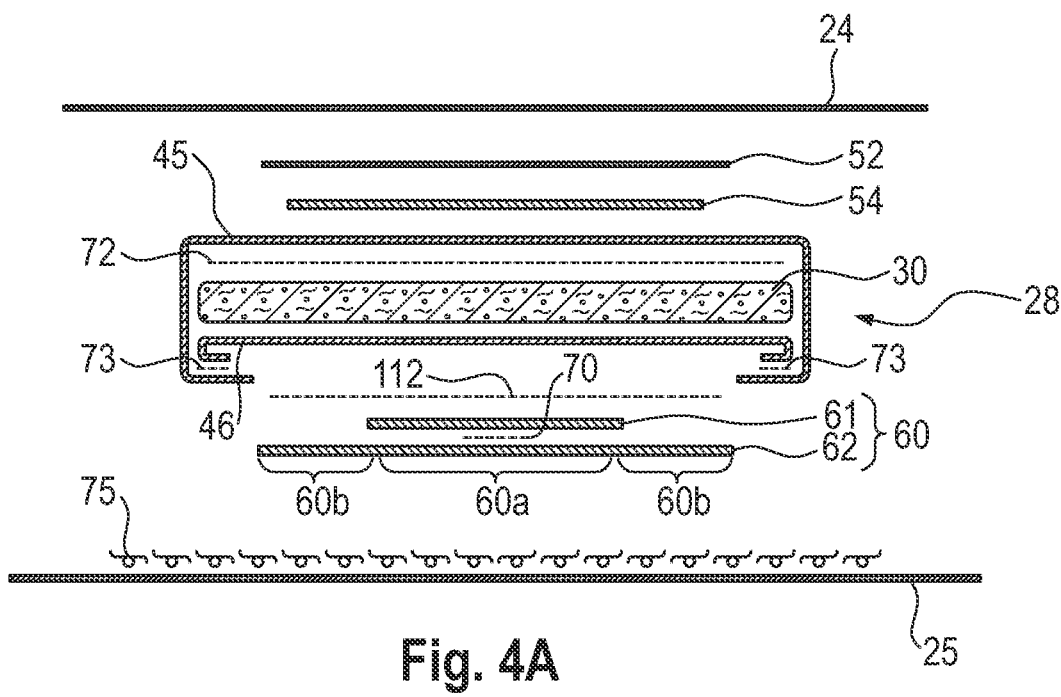
FIG. 4A-4B show an alternative construction of FIGS. 3A-3B with a different adhesive pattern between the core wrap and the cushion layer of FIG. 4A.
Figure 9:
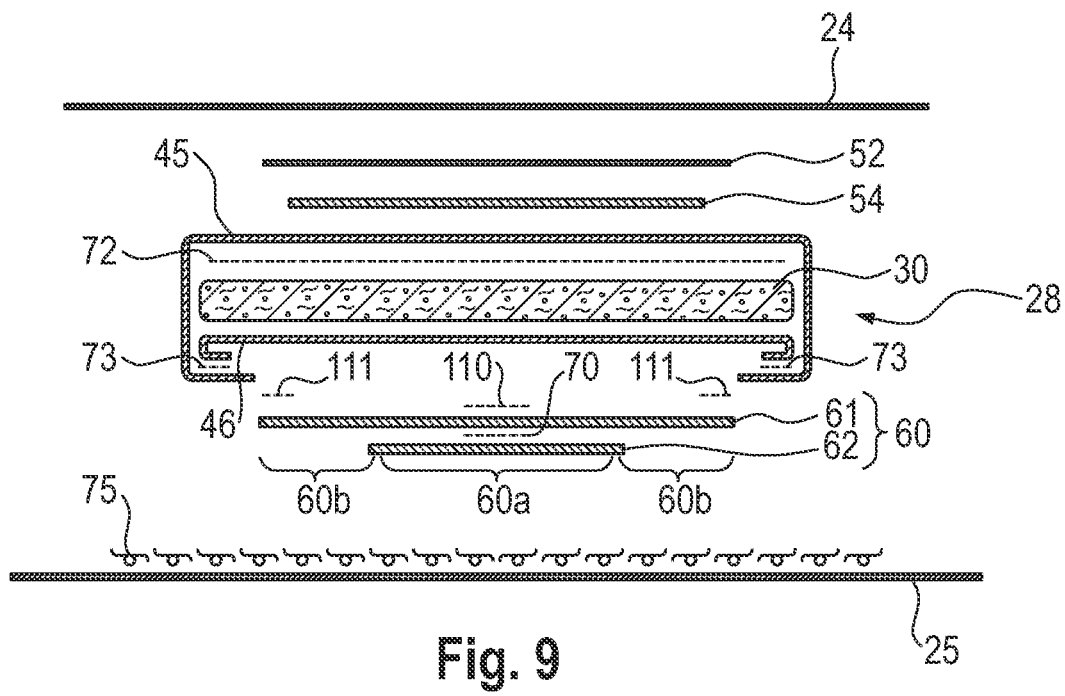

As shown in the example of FIG. 3A, the central area 60a of the cushion layer may be comprised of two sub-layers 61, 62, whereas the lateral areas 60b are comprised of a single sub-layer 62. Accordingly, the central area 60a may have twice the thickness and basis weight compared to the lateral areas 60b. The order according to which the sub-layers are stacked is not critical. For example, the narrow sub-layer 61 may be disposed above the larger sub-layer 62, as illustrated in FIG. 3A and FIG. 4A, or inversely the narrow sub-layer 61 may be disposed under the larger sub-layer 62, as illustrated in FIG. 9.

The width difference between the larger sub-layer 62 and the narrower sub-layer 61 may be chosen as desired. The ratio of the width of the cushion layer as a whole (i.e. for stacked layers the width of the larger layer 62) to the width of the narrower sub-layer 61 may for example range from 1.10 to 3.0, in particular from 1.4 to 2.5. This can provide a good balance between overall cushioning and material usage. For example, for a regular baby diaper, the width of the larger layer 62 may be 90 mm and the width of the narrower layer 61 maybe 50 mm, resulting in a ratio of 1.8.

Figure 5:
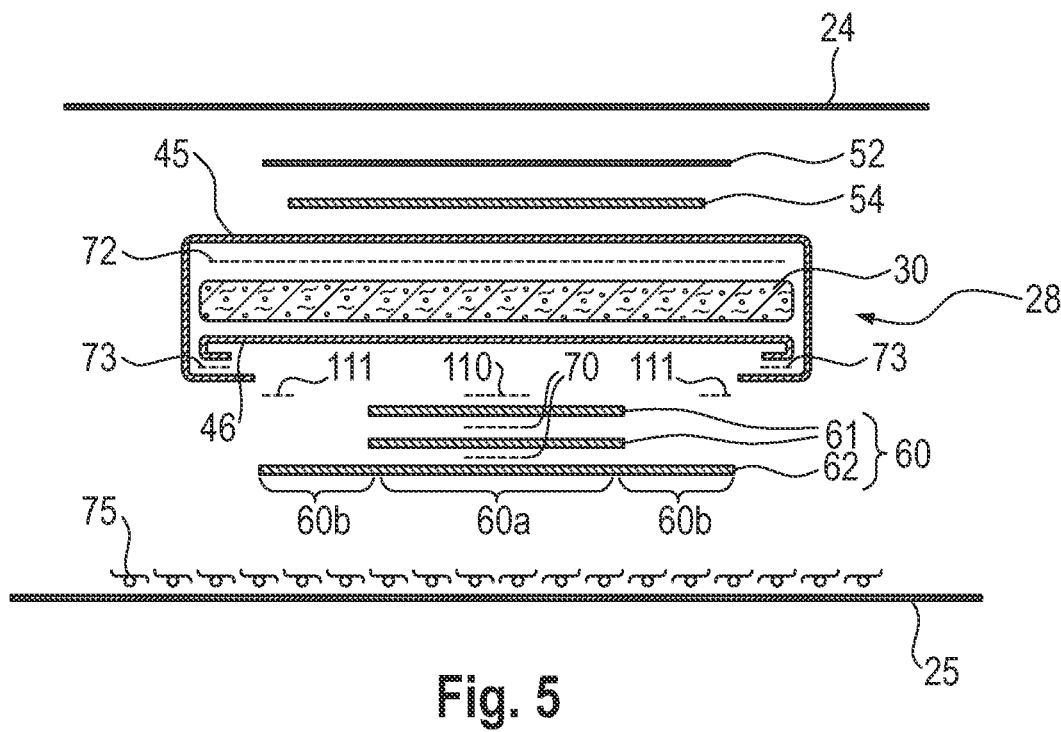
FIGS. 5-12 show alternative stacked multi-layer constructions.
Figure 6:
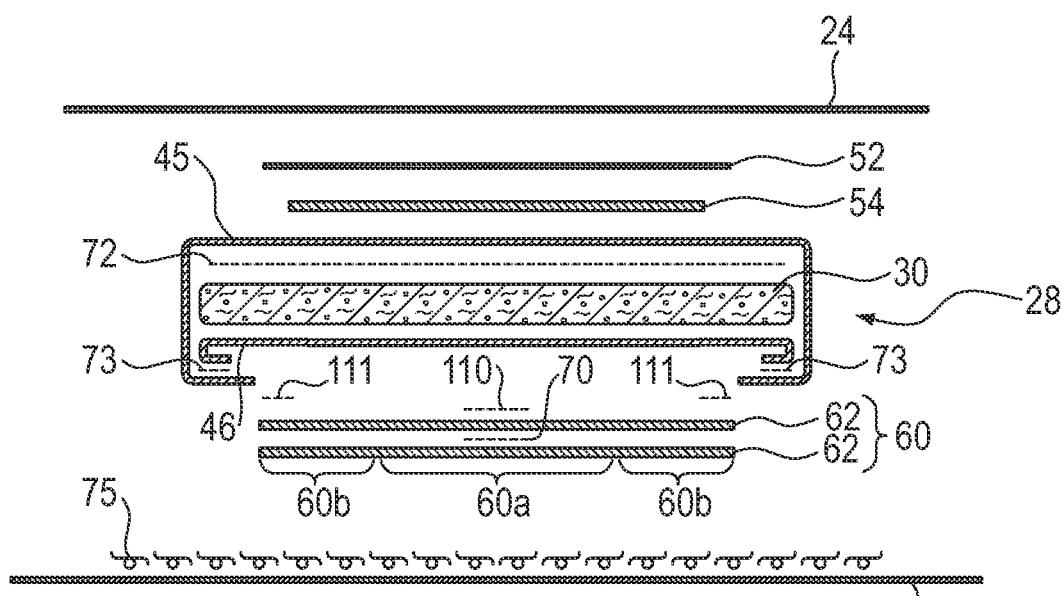
Figure 10:
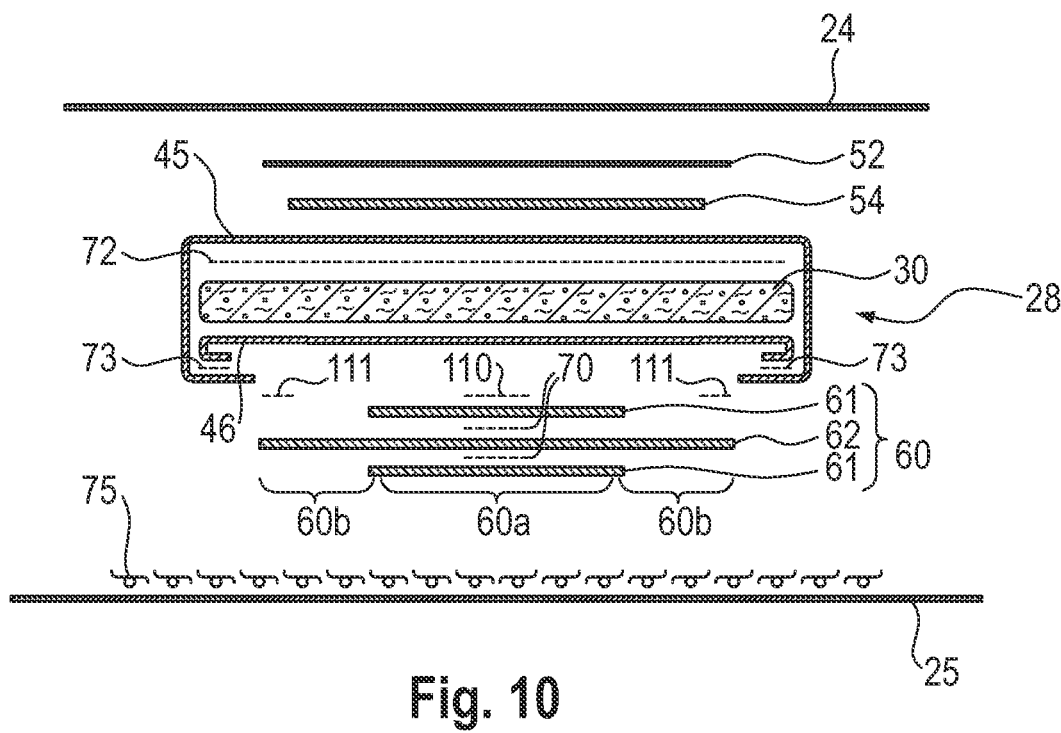

Other executions are of course possible, for example the cushion layer may comprise more than two sub-layers. The cushion layer may comprise two narrow layers 61 and one wide layer 62. The cushion layer central area 60a then has 3 times the basis weight and thickness compared to the lateral areas 60b. This is illustrated in FIG. 5 and FIG. 10 for example. The larger cushion layer may be disposed at the bottom of the stack, as represented in FIG. 5, or sandwiched between the two narrower sub-layers 61 as represented in FIG. 10.

Figure 11:
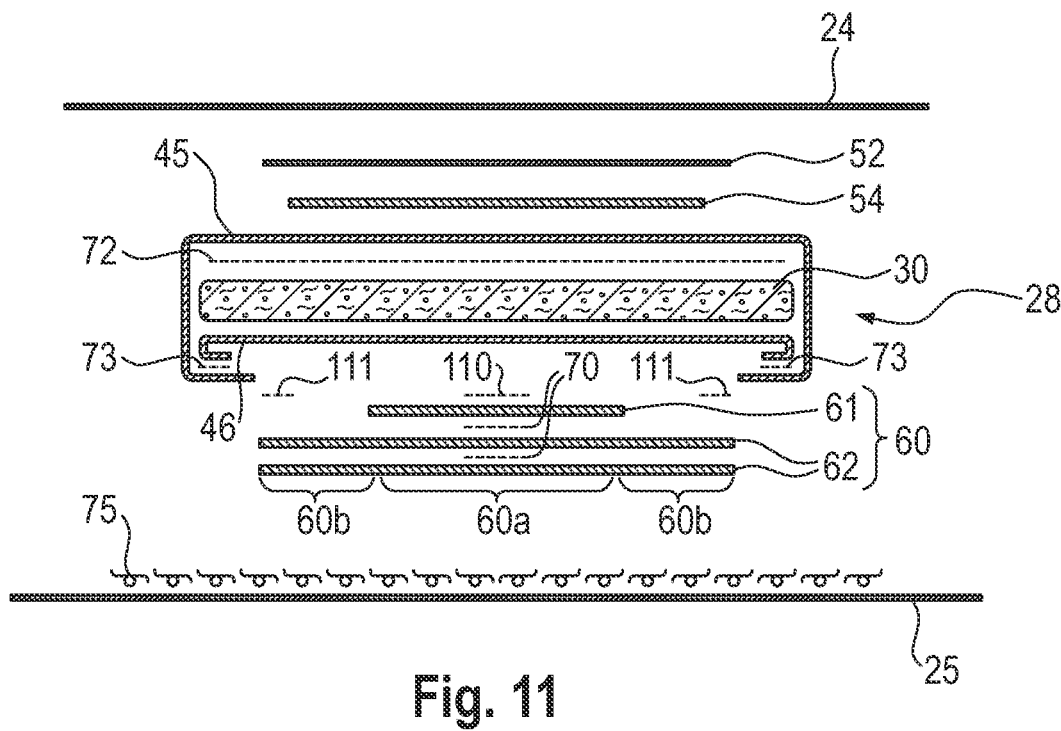
Figure 12:
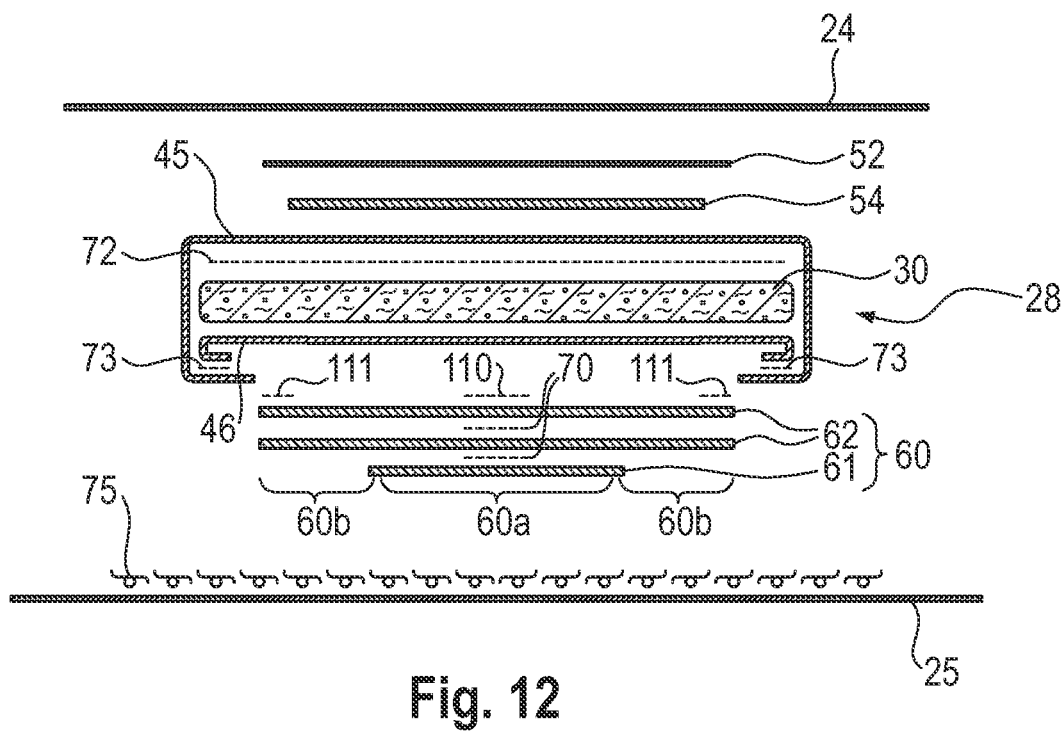

FIGS. 11 and 12 show further alternative stacking configuration, wherein the cushion layer comprises one narrow sub-layer 61 and two larger sub-layers 62. This provides a cushion layer having a basis weight and thickness in the central area 60a which is 3/2 the basis weight and thickness in the lateral areas 60b. FIG. 11 shows an example where the narrow sub-layer 61 is disposed on top of the stack, whereas FIG. 12 shows an example where the narrow 61 sub-layer is disposed at the bottom of the stack.

In general, the ratio R of the basis weight and thickness in the central area 60a of the cushion layer and the basis weight and thickness in the lateral area 60b is defined by the number of narrow sub-layer n1 and the number of large layers n2, according to the formula:

$$R=(n1+n2)/n2$$

The ratio R may typically be in the range of from 4/3 to 4/1, in particular 3/2 to 3/1.

The examples discussed so far where constructed by forming a stack of individual sub-layers, even if the sub-layers were typically formed by longitudinally slitting a single continuous web of cushion layer material during fabrication. The cushion layer 60 may also be provided by folding a single web of cushion layer material, so that a longitudinal slitting is not necessary. Two folding patterns may in particular be considered, the so-called Z-fold as illustrated on FIGS. 13-14, and the so-called omega fold, as illustrated in FIG. 15. In the Z-fold, the cushion web material 63 is folded along two longitudinally-extending fold lines so that it forms a central area 60a having three times the basis weight of the lateral areas 60b. In the Omega-fold configuration, the cushion web material 64 is folded along four longitudinally-extending fold lines, also resulting in a central area 60a having three times the basis weight of the lateral areas 60b. Of course, other fold constructions are possible, for example a Z-fold may be provided with 2 additional fold lines, resulting in a central area having 5 times the basis weight of the lateral areas 60b.

The first aspect of the invention as disclosed above may be combined or be independently practiced with a second aspect of the invention, that will be now described in further details below.

Second Aspect of the Invention

According to a second aspect of the invention, which may be combined with the first aspect, the at least two sub-layers are only partially attached to another, so that the sub-layers can partially decouple while still being maintained in a relatively stable position. The attachment area may be in an execution aligned along the longitudinal axis of the absorbent article.

It was found that the stiffness of the multi-layered cushion layer is reduced when the sub-layers are only partially attached to another, so that the sub-layers are at least partially free to move relative to one another. Higher stiffness in crotch region impacts fit and increases perception of crotch bulkiness and therefore crotch flexibility is more desired. In a "simplified" geometry, it is considered that the bending stiffness of the material goes with the cube of the caliper while for unbonded layers (in absence of friction), the increase in the bending stiffness grows linear with the number of layers. It is therefore "easier" to bend a collection of unbonded thinner layers. However completely unbonded sub-layers are not desirable, as this would drastically reduce the integrity and fit of the absorbent article.

The attachment area may be provided by known attachment means as known in the field. Adhesive bonding may be typically used to bond two adjacent sub-layers. As illustrated in FIG. 3a, the sub-layers 61,62 may be adhesively attached to another along a longitudinally-extending central attachment area 70 by a series of longitudinally extending glue stripes. The stripes may be provided by slot gluing, as is known in the art. For a regular diaper for example, 6 stripes each having 1 mm width with 1 mm gap between the slots, for a total central attachment area width of 11 mm may be used.

When more than two sub-layers are present, a partial attachment area 70 may be present between each pair of adjacent sub-layers, as exemplary shown in FIGS. 5, 8, 10, 11, 12. A centrally aligned partial attachment area is particularly useful when the sub-layers are individual stacked layers, as it provides for movement freedom for the lateral areas outside the central attachment area 70.

When the sub-layers are provided by a Z-fold configuration, the attachment areas 70', 70" may be aligned and adjacent with the folds, so that the folds are fixed in position and cannot un-fold during the production or the wear of the absorbent article. FIG. 13 shows a Z-folded cushion layer configuration, where the folding enables 3 times the basis weight in the central area 60a (e.g. 50 mm width) whereas the total width of folded cushion layer is 90 mm Small amount of longitudinally applied glue 70' is used to enable process feasibility. FIG. 14 shows a similar Z folded cushion layer configuration where wider glue slots 70" are used to ensure folds are intact during usage.

For the Omega fold configuration, a longitudinally-oriented central attachment area 70 may also be used. The attachment area may be typically about as long as the length of the sub-layers, or may be shorter if desired. The glue application may be continuous or intermittent, as is known in the art.

In an Omega fold cushion layer configuration, the Omega folding also enables 3 times the basis weight in the central area 60a (e.g. 50 mm width) compared to the lateral areas 60b (e.g. 90 mm width). A longitudinally-oriented central glue area 70, 110 at the bottom of the Omega folded cushion layers may be used to provide at the same for the partial attachment between the sub-layers, and a partial attachment to the lower substrate 46 of the core wrap. The Z-fold and Omega-fold configuration can be provided by relatively simple process point of view, and they do not require slitting of the cushion material web.

Third Aspect: Cushion Layer—Absorbent Core Bonding Pattern

Figure 3B:
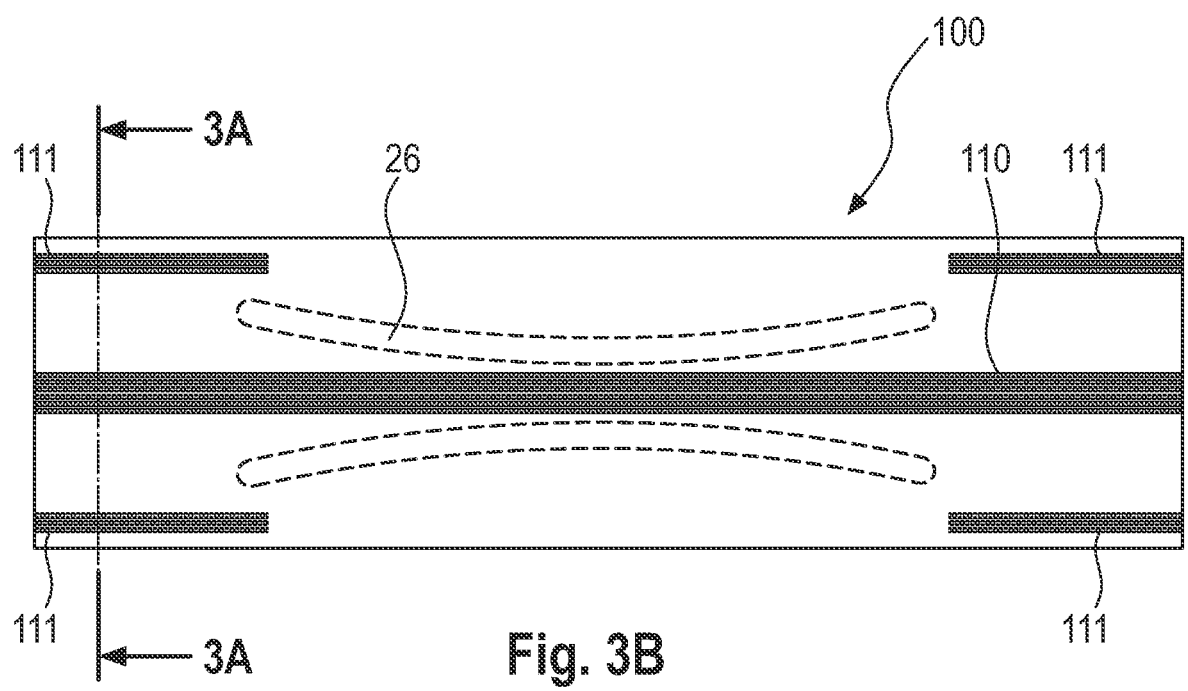
FIG. 3B is a plane view showing the adhesive pattern between the core wrap and the cushion layer of FIG. 3A.
Figure 4B:
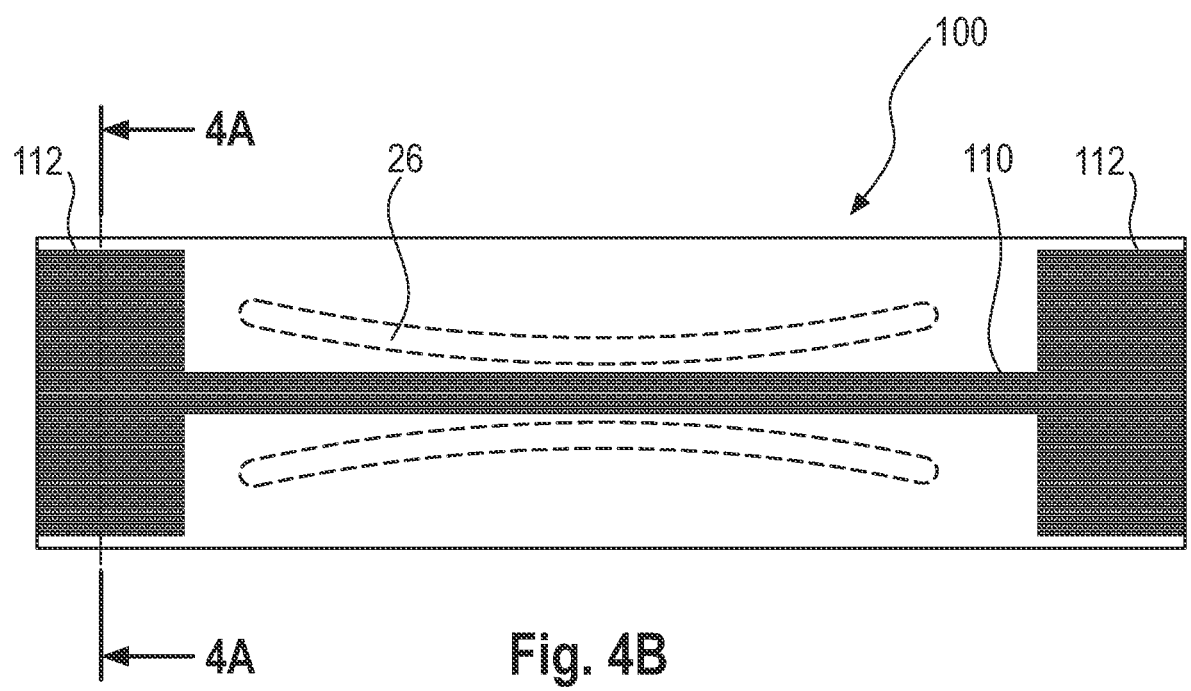

According to a third aspect of the invention, which may or may not be combined with the first or second aspect disclosed above, the wearer-facing side of the cushion layer 60 and the lower substrate layer 46 of the core wrap are only partially bonded to each other at their interface 100. Possible partial bonding patterns are illustrated in FIG. 3b and FIG. 4b respectively.

The interface 100 between the cushion layer 60 and the lower substrate 46 may thus comprise a bonded portion 110, 111 where the layers are bonded to each other, and a unbonded portion 120 where the cushion layer is not bonded to the core wrap's lower substrate. In the bonded portion, the two layers are preferably adhesively bonded. The inventors have found that partial bonding can reduce the transversal stiffness of the article compared to fully gluing the cushion layer to the absorbent core at their interface.

The bonded portion and the unbonded portion may each comprise several discrete zones. The bonded portion may in particular comprise a longitudinally-extending central zone 110, which at least partially overlaps with the longitudinal centerline of the article. The bonded portion may also comprise up to four corner bond zone(s) 111 disposed in each corner of the interface, as illustrated in FIG. 3B, or one or two transverse bond zone(s) 112 disposed adjacent the front and back edges respectively of the interface 100, as illustrated in FIG. 4B. The bonding pattern of FIG. 3B is partially represented in the FIGS. 4-15, but another bonding pattern such as the bonding pattern of FIG. 4B or a bonding pattern comprising only a longitudinally-extending central zone 110 may also be used in these examples.

Figure 7:
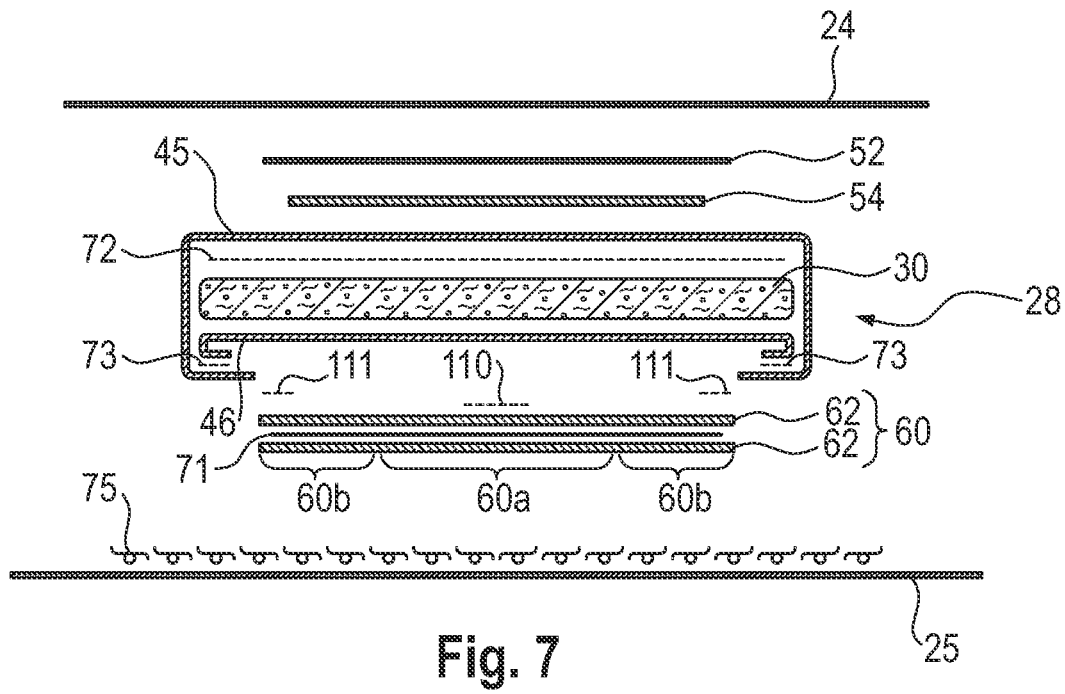
Figure 8:
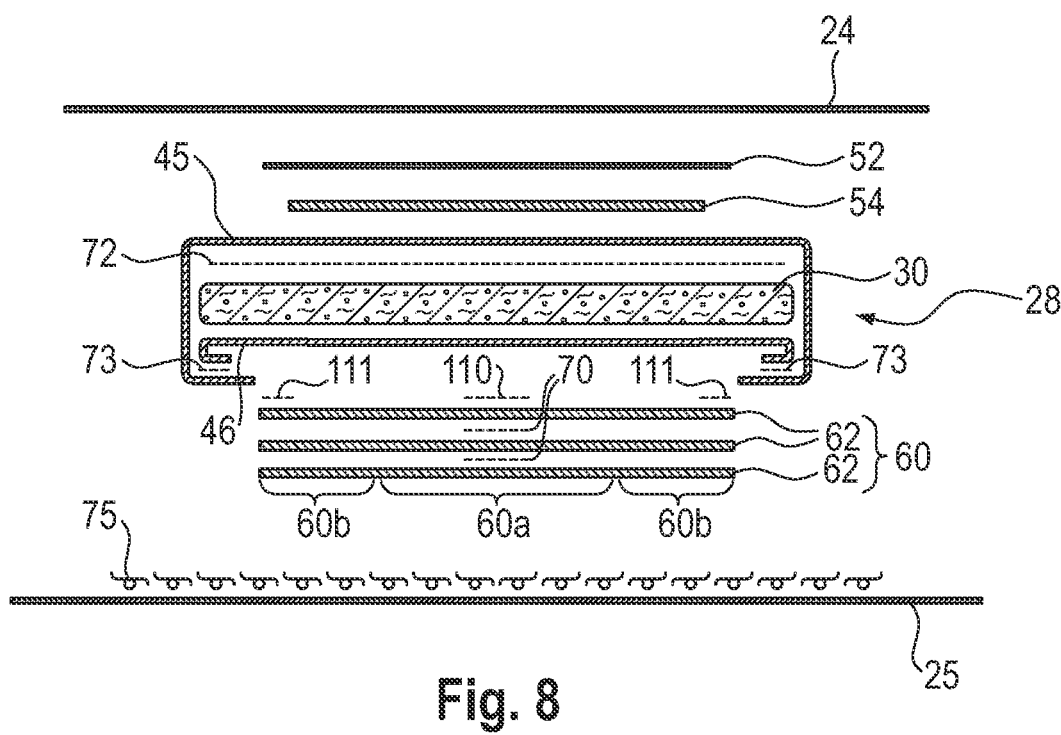

FIG. 7 shows an alternative embodiment of the third aspect of the invention where two equally large sub-layers are stacked and broadly attached together in face to face relationship by a broad attachment area 71, for example by spiral gluing or slot coating. While this embodiment does not have the advantages of the first and second aspects described above, it still provides an article having improved flexibility due to the partial bonding pattern at the interface 100 between the top side of the cushion layer and the lower substrate core wrap.

Cushion Layer Material

The material forming the cushion layer 60 may be comprised or consists of a nonwoven layer, but other materials are not excluded. Nonwoven layers are commonly used in absorbent articles and can be slit longitudinally, cut transversally, disposed and attached in the absorbent article using conventional techniques.

Commonly used fiber materials (PE, PP, PET, coPET, Bico, or mixes of those fibers within others) may be used. The individual fibers or the nonwoven as a whole can be treated to enhance specific fluid handling characteristics such as fluid permeable layers or fluid impermeable barriers, if desired.

The cushion layer may also serve as a temporary reservoir or as a lower acquisition and distribution layer for liquid that has flown through the absorbent material because it was not absorbed fast enough by the absorbent material of the layer of absorbent material. Alternatively, the material forming the cushion layer may be selected to be substantially liquid impermeable (hydrophobic) to provide a further liquid barrier on the garment-facing side of the article.

Additional layers provided to an absorbent article generally increase the thickness and bulk of the article, thereby reducing wearer comfort. Also, increased bulk is generally not desirable, especially between the wearer's legs. Therefore, it may be desirable to limit the caliper of the cushion layer to be in the range of from 0.4 mm and up to 4 mm, e.g. in the range of 0.5 mm to 2 mm, as measured at 0.85 kPa pressure according to the Caliper Measurement Method described herein. The caliper is measured in the thickest region of the cushion layer, which is typically the central region 60a where the maximum numbers of sub-layers are present, either as a stack or a folded layer.

The basis weight of the sub-layer may typically be the same of each sub-layer, but other configuration are possible. Typically, each sub-layer may have a basis weight comprised in the range of from 10 g/m$^2$ to 40 g/m$^2$. The basis weight of the cushion layer where the maximum numbers of sub-layers are present, either as a stack or a folded layer, may typically be in the range of from 24 g/m$^2$ to 100 g/m$^2$, but other values are possible, e.g. from 30 g/m$^2$ to 80 g/m$^2$.

The basis weight of the sub-layer is typically homogeneous throughout the length and width of the cushion layer (i.e. in the longitudinal and transverse direction). The basis weight of a material is typically known from the supplier of the cushion material used. If an unknown material is used, it can be calculated by dividing the weight of the cushion layer by its surface for the area considered, as is known in the art.

The cushion layer is preferably free of superabsorbent polymer particles. Carded nonwovens (made of staple fibers) were found particularly suitable. Carded nonwovens may be calendar bonded or air-through bonded, as is known in the art. The nonwoven layer may also be a spunbond or meltblown nonwoven web (made of continuous fibers) or a nonwoven with spunbond and meltblown layers (e.g. an SMS, SMMS, SMSS, SSS, SSSS or the like).

Air-through bonded nonwoven generally have high loft. Hence, they have a porous structure to provide void volume for absorbing and temporarily holding liquid. At the same time, they provide softness and do not have an excessively high bending stiffness.

The cushion layer may comprise at least 30 weight %, optionally at last 50% and up to 100 weight % of crimped fibers based on the total weight of the cushion layer. The crimped fibers may have two-dimensional crimp, three dimensional crimp or a combination of two- and three-dimensional crimp. Typically, in the carded process, all or most fibers are two-dimensionally crimped (zigzag), whereas eccentric bicomponent fibers may be typically three-dimensional crimped. Crimped fibers may help driving the bulkiness and void volume of the nonwoven.

The cushion layer, and in particular its constituent sub-layers, may be made or comprise of synthetic fibers. Particularly suitable synthetic fibers are made of polyolefins (e.g. polyethylene, polypropylene or mixtures or combinations thereof), polyethylene terephthalate (PET), co-PET, polylactic acid (PLA), polyhydroxy alkanoid (PHA), or combinations or mixtures thereof. The fibers may be continuous or staple fibers. The fibers may be monocomponent fibers or multicomponent fibers, such as bicomponent fibers. If the fibers comprised by the cushion layer are bicomponent fibers, they have a core-sheath configuration, wherein the core component has a higher melting point than the sheath component.

The fibers comprised by the cushion layer are preferably staple fibers. Similar to a nonwoven web made of continuous fibers, a nonwoven web of staple fibers is preferably air-through bonded. In addition to hydroentanglement (spunlace) or air-through bonding, the nonwoven web of staple fibers may or may not have undergone some localized bonding with heat and/or pressure (e.g. point bonding/calendar bonding), introducing localized bond regions where the fibers are fused to each other.

Irrespective of whether the nonwoven web is made of continuous fibers or staple fibers, the localized bonding should however not bond an excessively large surface area, thus negatively impacting the loft and void volume of the nonwoven web. Preferably, the total bond area obtained by localized bonding with heat and/or pressure (in addition to hydroentanglement or air-through bonding) should not be more than 20%, or not be more than 15%, or not be more than 10% of the total surface area of the nonwoven web.

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The air velocity is typically between 30 and 90 meter per minute and the dwell time may be as long as 6 seconds. The melting and re-solidification of the polymer provide the bonding between different fibers.

The hot air melts the staple or continuous fiber, or, for multicomponent fibers, the lower melting polymer component of the fiber and thereby forms bonds between the staple fibers to consolidate and integrate the layer of staple fibers into a web.

The nonwoven layer comprised by or forming the cushion layer may comprise multicomponent fibers. The fibers of the nonwoven may comprise at least 30 weight-%, or at least 40 weight-%, or at least 50 weight-%, or at least 70 weight-%, or at least 90 weight-% or 100 weight-% of multicomponent fibers based on the total weight of the nonwoven comprised by the lower acquisition and distribution layer. The multicomponent fibers may be bicomponent fibers, such as core-sheath or side-by-side bicomponent fibers.

Alternatively, the nonwoven layer may comprise monocomponent fibers. The fibers of the nonwoven comprised by the lower acquisition and distribution layer, may comprise at least 30 weight-%, or at least 40 weight-%, or at least 50 weight-%, or at least 70 weight-%, or at least 90 weight-% or 100 weight-% of monocomponent fibers based on the total weight of the nonwoven comprised by the lower acquisition and distribution layer. The nonwoven web comprised by or forming the cushion layer may comprise a mixture of monocomponent fiber and multicomponent fibers.

The cushion layer when used as a lower acquisition and distribution layer may comprise a hydrophilic agent, especially if the cushion layer comprise or consists of synthetic fibers that are inherently hydrophobic. Any conventional hydrophilic treatments may be used to provide the hydrophilic agent. Typically, a web such as a nonwoven can be externally coated by a surfactant directly or via an oil/emulsion. Alternatively, hydrophilic melt additives can be added in the polymer melt used to make the fibers, as is known in the art. Hydrophilic melt additives are amphiphilic molecules having a hydrophilic head and a hydrophobic tail. The hydrophilic head is oriented towards the surface of the adhesive, thus providing for the hydrophilic character of the adhesive, while the hydrophobic head remains in the polymer matrix. The lower acquisition and distribution layer 60 and the lower substrate layer 46 may then advantageously be both hydrophilic. The lower acquisition and distribution layer may be optionally less hydrophilic than the lower substrate layer.

Other Considerations

The cushion layer 60 as a shole may typically have an overall surface which is the same or smaller than the surface of the core wrap. The cushion layer may be advantageously disposed so that it covers selected areas of the absorbent core, in particular at least a portion the crotch region of the absorbent article, instead of a full coverage of the absorbent core. The cushion layer typically has a basis weight at least equal and typically higher than the basis weight of the core wrap layer. According to a first aspect, the cushion layer may have a basis weight of more than 20 g/m². According to a further aspect, at least 50% of the surface of the garment-facing side of the cushion layer may be bonded directly or indirectly to the backsheet, especially in area(s) vertically corresponding to the channels 26.

The absorbent core may optionally comprise at least one channel within the absorbent layer that is substantially free of absorbent material. The channel forms a three-dimensional channel in use when the absorbent layer swells after absorbing a liquid such as urine. The upper substrate 45 and the lower substrate 46 side of the absorbent core wrap may in particular be bonded to each other in the channel area(s). The cushion layer can advantageously be decoupled from the core wrap lower substrate 46 in the channel area(s).

Packages

A plurality of articles according to the invention may be packaged in a package for transport and sale. At least 50% of the articles, and preferably all the articles, in the package may be according to the invention. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate number of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression are sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 65 mm to 110 mm, from 70 mm to 110 mm, from 75 mm to 105 mm, or from 80 mm to 100 mm, specifically reciting all 0.1 mm increments within the specified ranges and all ranges formed therein or thereby, according to the In-Back Stack Height Test described herein.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in US2019/0192723, published on Jun. 27, 2019.

TEST METHODS

Caliper Measurement Method

The caliper of a layer such as the cushion layer is determined using the Caliper Measurement Method. In the Caliper Measurement Method, two flat, parallel surfaces are used to apply unidirectional pressure to both sides of a substrate specimen, and the resulting separation between the parallel surfaces is measured. All measurements are performed in a laboratory maintained at 23±2° C. and 50±2% relative humidity and test specimens are conditioned in this environment for at least 2 hours prior to testing.

One suitable example of apparatus for use in the Caliper Method is a Mitutoyo Digimatic Series 543 ID-C digital indicator (Mitutoyo America Corp., Aurora, Illinois, USA), or equivalent, fitted with a circular flat "foot" having a diameter of 4.0 cm at the end of the moving shaft of the indicator gauge. The indicator is mounted on a horizontal granite base such that the shaft of the indicator gauge is oriented vertically and the plane of the circular foot is parallel to the granite base. The circular foot is sized and weighted such that the gravitational force associated with the mass of the foot and the indicator shaft together divided by the area of the circular foot constitutes 0.85 kPa of downward pressure from the circular foot on the granite base. Specimens at least as large as the circular foot are analyzed between the circular foot and granite base. The caliper is measured 20 s after the round foot has been contacted with the specimens. For a given material, 10 specimens are measured and the average value reported as the caliper of the material.

In-Bag Stack Height

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within +0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 gram.

Test Procedure

Absorbent article packages are equilibrated at 23±2° C. and 50±2% relative humidity prior to measurement.

The horizontal sliding plate is raised and an absorbent article package is placed centrally under the horizontal sliding plate in such a way that the absorbent articles within the package are in a horizontal orientation (see FIG. 14 of WO2021118904_A1). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within +0.5 mm ten seconds after releasing the horizontal sliding plate. Five identical packages (same size packages and same absorbent articles counts) are measured and the arithmetic mean is reported as the package width. The "In-Bag Stack Height"= (package width/absorbent article count per stack)×10 is calculated and reported to within +0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene, having a longitudinal centerline and a transversal centerline, the absorbent article comprising:
    a liquid-permeable topsheet;
    a liquid-impermeable backsheet;
    an absorbent core between the topsheet and the backsheet,
        wherein the absorbent core comprises an absorbent material disposed between an upper substrate layer and a lower substrate layer forming a core wrap;
    wherein the absorbent material comprises at least 50% superabsorbent polymers by weight of the absorbent material; and
    a cushion layer disposed between the absorbent core and the backsheet;
        wherein the cushion layer comprises at least two sub-layers, and wherein the sub-layers are arranged so that the cushion layer has a higher basis weight in a longitudinally-extending central area relative to lateral areas disposed transversally outwardly of the central area.

2. The absorbent article according to claim 1, wherein at least two of the sub-layers have different widths so that the cushion layer comprises a longitudinally-extending central area having a higher basis weight than a basis weight of the lateral areas disposed transversally outwardly of the central area.

3. The absorbent article according to claim 2, wherein a ratio of the width of the cushion layer as a whole to the width of the central area is in the range from about 1.10 to about 3.0.

4. The absorbent article according to claim 3, wherein a ratio of the basis weight of the central area to a basis weight in the lateral areas is in the range from about 4/3 to about 4/1.

5. The absorbent article according to claim 1, wherein at least some or all of the sub-layers are stacked individual sub-layers.

6. The absorbent article according to claim 1, wherein at least some or all of the sub-layers are formed by folding a single cushion material layer in a configuration selected from a Z-fold or an Omega-fold.

7. The absorbent article according to claim 1, wherein the sub-layers have the same length.

8. The absorbent article according to claim 1, wherein the absorbent material comprises at least one layer of superabsorbent polymer particles which is free of cellulose fibers, the superabsorbent polymer particles being immobilized by a fibrous net of an adhesive or a thermoplastic polymer.

9. The absorbent article according to claim 1, wherein the sub-layers are made of the same cushion material.

10. The absorbent article according to claim 1, wherein at least one of the sub-layers has a caliper of at least 0.2 mm, as measured at 0.85 kPa pressure, and a basis weight of at least 12 gsm.

11. The absorbent article according to claim 1, wherein a caliper of the cushion layer in its thickest region is at least 0.4 mm, as measured at 0.85 kPa pressure.

12. The absorbent article according to claim 11, wherein a basis weight of the cushion layer in the thicker region is in the range of from about 24 $g/m^2$ to about 100 $g/m^2$.

13. An absorbent article for personal hygiene, having a longitudinal centerline and a transversal centerline, the absorbent article comprising:
   a liquid-permeable topsheet;
   a liquid-impermeable backsheet;
      an absorbent core between the topsheet and the backsheet, wherein the absorbent core comprises an absorbent material disposed between an upper substrate layer and a lower substrate layer forming a core wrap;
   wherein the absorbent material comprises at least 50% superabsorbent polymers by weight of the absorbent material; and
   a cushion layer disposed between the absorbent core and the backsheet;
   wherein the cushion layer comprises at least two sub-layers, and wherein two vertically adjacent sub-layers are partially attached to each other by one or more longitudinally-extending attachment areas, and wherein the one or more longitudinally-extending attachment areas is a longitudinally-extending central attachment area aligned with the longitudinal axis of the absorbent article, so that the cushion layer comprises two lateral non-attachment areas disposed laterally outwardly of this central attachment area where the sub-layers are decoupled of another.

14. The absorbent article according to claim 13, wherein the longitudinally-extending attachment area is an adhesive attachment area.

15. The absorbent article according to claim 13, wherein at least one of the sub-layers is a nonwoven.

16. The absorbent article according to claim 15, wherein at least one of the sub-layers is a carded nonwoven.

* * * * *